(12) United States Patent
Ziegler et al.

(10) Patent No.: US 8,747,900 B2
(45) Date of Patent: *Jun. 10, 2014

(54) DOSAGE FORM WITH IMPROVED RELEASE OF CEFUROXIMAXETIL

(75) Inventors: Iris Ziegler, Roetgen (DE); Andreas Fischer, Huertgenwald (DE)

(73) Assignee: Gruenenthal GmbH, Aachen (DE)

( * ) Notice: Subject to any disclaimer, the term of this patent is extended or adjusted under 35 U.S.C. 154(b) by 347 days.

This patent is subject to a terminal disclaimer.

(21) Appl. No.: 11/912,627

(22) PCT Filed: Apr. 25, 2006

(86) PCT No.: PCT/EP2006/003814
§ 371 (c)(1),
(2), (4) Date: Oct. 25, 2007

(87) PCT Pub. No.: WO2006/114277
PCT Pub. Date: Nov. 2, 2006

(65) Prior Publication Data
US 2008/0187594 A1    Aug. 7, 2008

(30) Foreign Application Priority Data
Apr. 25, 2005  (DE) .................. 10 2005 019 458

(51) Int. Cl.
| A61K 9/16 | (2006.01) |
| A61K 9/50 | (2006.01) |
| A01N 59/26 | (2006.01) |
| A61K 33/42 | (2006.01) |
| A61K 9/54 | (2006.01) |
| A61K 31/545 | (2006.01) |

(52) U.S. Cl.
USPC ............ 424/490; 424/602; 424/458; 514/200

(58) Field of Classification Search
USPC .......................................................... 424/490
See application file for complete search history.

(56) References Cited

U.S. PATENT DOCUMENTS

| 3,974,153 | A |   | 8/1976 | Cook et al. |
| 4,267,320 | A |   | 5/1981 | Gregson et al. |
| 4,562,181 | A |   | 12/1985 | Crisp et al. |
| 4,865,851 | A |   | 9/1989 | James et al. |
| 5,063,224 | A |   | 11/1991 | Mosher et al. |
| 5,292,461 | A | * | 3/1994 | Juch et al. .................. 264/37.29 |
| 5,356,625 | A | * | 10/1994 | Ying ............................ 424/94.1 |
| 5,677,443 | A | * | 10/1997 | Zenoni et al. ................ 540/215 |
| 6,346,530 | B1 | * | 2/2002 | Somani et al. ............. 514/226.8 |
| 6,372,255 | B1 |   | 4/2002 | Saslawski et al. |
| 2002/0119195 | A1 | * | 8/2002 | Sen et al. ...................... 424/471 |
| 2003/0072798 | A1 | * | 4/2003 | Schwarz ....................... 424/456 |
| 2003/0161888 | A1 |   | 8/2003 | Fernandez et al. |
| 2003/0228334 | A1 | * | 12/2003 | Mercier et al. ................ 424/401 |
| 2005/0079200 | A1 |   | 4/2005 | Rathenow et al. |
| 2005/0079201 | A1 |   | 4/2005 | Rathenow et al. |
| 2006/0088592 | A1 | * | 4/2006 | Choi et al. .................... 424/464 |
| 2007/0125247 | A1 |   | 6/2007 | Kunstmann et al. |

FOREIGN PATENT DOCUMENTS

| DE | 27 06 413 A1 | 8/1977 |
| DE | 34 27 828 A1 | 2/1985 |
| DE | 38 16 464 C3 | 11/1988 |
| DE | 202 18 068 U1 | 4/2003 |
| DE | 102 54 412 A1 | 6/2003 |
| DE | 698 07 747 T2 | 6/2003 |
| DE | 20 2004 009 060 U1 | 9/2004 |
| DE | 103 33 098 A1 | 2/2005 |
| DE | 103 33 099 A1 | 2/2005 |
| DE | 103 51 150 A1 | 5/2005 |
| EP | 0 107 276 A2 | 5/1984 |
| EP | 0 280 571 B1 | 8/1988 |
| EP | 0 665 009 A1 | 8/1995 |
| EP | 0 757 991 A1 | 2/1997 |
| EP | 0 937 727 A1 | 8/1999 |
| GB | 1 571 683 | 7/1980 |
| GB | 2 145 409 A | 3/1985 |
| WO | WO 02/06289 A1 | 1/2002 |
| WO | WO 03/079957 A1 | 10/2003 |
| WO | WO 04/000202 A1 | 12/2003 |
| WO | WO 04/000264 A1 | 12/2003 |
| WO | WO 2004/019901 A2 | 3/2004 |
| WO | WO 2004/101017 A2 | 11/2004 |
| WO | WO 2005/006286 A1 | 1/2005 |
| WO | WO 2005/042045 A1 | 5/2005 |
| WO | WO 2005/065658 A1 | 7/2005 |

OTHER PUBLICATIONS

Remington, The Science and Practice of Pharmacy, 1885, p. 1-3.*
Guidance for Industry,"Waiver of in Vivo Bioavailability and Bioequivalence Studies for Immediate-Release Solid Oral Dosage Forms Based on a Biopharmaceutics Classification System", U.S. Department of Health and Human Services Food and Drug Administration Center for Drug Evaluation and Research (CDER), 2000, (six (6) pages).
Yoshitaka Uno et al., "Molecular Weight Distribution of Carrageenans Studied by a Combined Gel Permeation/Inductively Coupled Plasma (GPC/ICP) Method", Food Additives and Contaminants, 2001, vol. 18, No. 9, pp. 763-772.
Andre S. Raw et al. "Regulatory considerations of pharmaceutical solid polymorphism in Abbreviated New Drug Applications (ANDAs)", Advanced Drug Delivery Reviews, Feb. 23, 2004, pp. 397-414, vol. 56, No. 3.
Irena Oszczapowicz et al. "Esters of Cephalosporins. Part II. Differences in the Properties of Various Forms of the 1-Acetoxyethyl Ester of Cefuroxime", ACTA Poloniae Pharmaceutica, Polish Pharmaceutical Society, Warzsaw, PI, Drug Research, vol. 52, No. 5, 1995, pp. 397-401.

(Continued)

Primary Examiner — Brian-Yong Kwon
Assistant Examiner — Mark V Stevens
(74) Attorney, Agent, or Firm — Crowell & Moring LLP

(57) ABSTRACT

The invention relates to a pharmaceutical composition comprising cefuroximaxetil and at least one carrageenan selected from the group consisting of κ-carrageenan, λ-carrageenan and ι-carrageenan. The invention furthermore relates to pellets, to a multiparticulate, pharmaceutical dosage form and to a novel crystalline modification of cefuroximaxetil.

13 Claims, 2 Drawing Sheets

(56) References Cited

OTHER PUBLICATIONS

Irena Oszczapowicz et al. "Esters of Cephalosporins. Part VI. Properties of the γ-Form of 1-Acetoxyethyl Ester of Cefuroxime", ACTA Poloniae Pharmaceutica, May-Jun. 1998, vol. 55, No. 3, pp. 197-204.
Seoung Wook Jun et al. "Cefuroxime axetil solid dispersions prepared using solution enhanced dispersion by supercritical fluids", Journal of Pharmacy and Pharmacology, London, GB, vol. 57, No. 12, Dec. 2005, pp. 1529-1537.
International Search Report dated Mar. 9, 2007 with English translation of relevant portion (Seventeen (17) Pages).
German Search Report dated Jul. 6, 2007 with English translation of relevant portion (Eight (8) Pages).
Form PCT/IPEA/416, PCT/IPEA/409 (Thirteen (13) Pages), Aug. 28, 2007.
Form PCT/IB/338 and Form PCT/IPEA/409 (Thirteen (13) Pages), Apr. 24, 2008.
David E. Bugay et al., "Pharmaceutical Excipients", Drugs and the Pharmaceutical Sciences, Table of Contents, vol. 94, 1998, (nine (9) pages).
T. H. M. Snoeren, "Kappa-Carrageenan—A Study on its Physico-Chemical Properties, Sol-Gel Transition and Interaction with Milk Proteins", H. Veenman & Zonen B.V.—Wageningen, Table of Contents, 1976, (fifty-eight (58) pages).
Fielder, "Fuer Pharmazie, Kosmetik and Angrenzende Gebiete", 2002, (three (3) pages).

\* cited by examiner

DOSAGE FORM WITH IMPROVED RELEASE OF CEFUROXIMAXETIL

BACKGROUND OF THE INVENTION

The invention relates to a pharmaceutical composition which contains cefuroximaxetil and ensures improved release of the active ingredient from dosage forms. The invention also relates to a stable crystalline modification of cefuroximaxetil.

Cefuroximaxetil (ATC code J01DA45) is broad spectrum antibiotic of the cephalosporin class which is conventionally administered orally. Administration of cefuroximaxetil is indicated in infections of the airways, of the urogenital tract and in otorhinolaryngeal infections. It may also be administered in soft tissue infections and infections of the bones and joints (c.f. L. J. Scott et al., Drugs 2001, 61, 1455-1500).

Cefuroximaxetil is the 1-acetoxyethyl ester of cefuroxime, i.e. of (6R,7R)-3-carbamoyloxymethyl-7-[(Z)-2-(fur-2-yl)-2-methoxyiminoacetamido]ceph-3-em-4-carboxylic acid (c.f. U.S. Pat. No. 3,974,153 and U.S. Pat. No. 4,267,320; ATC code J01DA06). Where approved for pharmaceutical use, cefuroximaxetil conventionally comprises a mixture of two diastereomers. Processes for isolating the individual diastereomers are described in the prior art (c.f. DE-OS-27 06 413 and U.S. Pat. No. 5,063,224).

For the purposes of the description, cefuroximaxetil preferably comprises the pharmaceutically usable mixture of the diastereomers, as is for example defined in USP 23, pages 315/316. The two diastereomers are here present in an approx. 1:1 ratio. According to USP 23, a sample of the mixture of diastereomers is chromatographed. A peak $r_A$ then corresponds to the A isomer and a peak $r_B$ to the B isomer. According to USP 23, page 315, right hand column, the ratio of the diastereomers is then determined using the formula $r_A/(r_A+r_B)$. This ratio must be between 0.48 and 0.55.

The production of dosage forms which are suitable for administering cefuroximaxetil is associated with various problems. On the one hand, these problems are attributable to the chemical and physical properties of the active ingredient, in particular to its bitter flavour and its comparatively poor solubility, which is largely pH-independent in an aqueous medium. On the other hand, however, the physical properties of conventional solid dosage forms, in particular their rate of disintegration under physiological conditions also play an important part.

One substantial problem which is directly attributable to the properties of the active ingredient itself is the only slight solubility of cefuroximaxetil in an aqueous medium. It is particularly unfavourable in this connection that this slight solubility prevails not only in gastric juice, but also at pH values which correspond to the physiological pH values of the small intestine. It is precisely in the small intestine that cefuroximaxetil should in principle be as rapidly available as possible, as this is largely where it is absorbed.

The bioavailability of cefuroximaxetil is inter alia a function of its solubility. USP 23 describes a test on page 316 for determining the bioavailability of cefuroximaxetil. To this end, the solubility of the active ingredient from a standardised tablet formulation is determined in methanol. Those products in which at least 60% of the active ingredient is dissolved in 15 minutes and at least 75% of the active ingredient is dissolved within 45 minutes are approved.

Various solid modifications of cefuroximaxetil are known in the prior art which are distinguished inter alia by different solubility.

The amorphous form of cefuroximaxetil is conventionally used for the production of oral dosage forms (c.f. DE-OS 34 27 828, EP-A 107 276 and U.S. Pat. No. 4,562,181). However, use of the amorphous form is problematic. It is accordingly known that at 37° C. amorphous cefuroximaxetil forms a sparingly soluble gel layer on the external surface of the particles when it comes into contact with water, so considerably delaying active ingredient release.

Apart from the amorphous form of cefuroximaxetil, various crystalline modifications of cefuroximaxetil are known. It has been reported that these crystalline modifications have a lesser tendency to form a gel than the amorphous form. However, in comparison with the amorphous form, hitherto known crystalline modifications exhibit lower solubility and thus also reduced bioavailability.

GB-A-15 71 683 accordingly discloses a modification which is hereinafter denoted the "α-modification". An IR spectrum is disclosed in GB-A-21 45 409. The α-modification does not exhibit sufficient bioavailability for use as a pharmaceutical preparation; when tested according to USP 23, it does not achieve the specified minimum solubility. EP-A-757 991 discloses a modification which is hereinafter denoted the "β-modification". However, when determined in accordance with the standard method according to USP 23 page 316, the solubility of the active ingredient only amounts to somewhat over 40% after 45 minutes. EP-A-937 727 discloses a modification which is hereinafter denoted the "γ-modification". According to the disclosure of the document, 73.0% of the active ingredient are dissolved after 45 minutes (determined in accordance with the standard method according to USP 23, page 316). EP-A-937 727 furthermore discloses a hemihydrate which consists to an extent of approx. 95% of the R isomer.

Apart from its slight solubility, the bitter flavour of cefuroximaxetil also plays a part when formulating oral dosage forms.

Cefuroximaxetil is accordingly conventionally marketed in the form of film coated tablets (Elobact® and Zinnat®), which according to the manufacturers' instructions should not be crushed or chewed due to the bitter flavour of cefuroximaxetil. Other dosage forms are thus recommended for children below 5 years of age. Cefuroximaxetil is, for example, also marketed as a powder for suspension, the active ingredient being provided as a dry granular product. Shortly before the preparation is first taken, water is added to produce a suspension which can be stored in a refrigerator (+2° C. to +8° C.) for 10 days. Currently marketed powders for suspension contain a granular product of amorphous cefuroximaxetil, which is coated with stearic acid in order to mask the bitter flavour of the active ingredient (c.f. DE-OS-38 16 464). Despite the coating, this formulation still has an unpleasant, bitter flavour and so does not always meet with unreserved acceptance from children. The flavour even gets worse during storage of the suspension, as the coating softens over time. Furthermore, the bioavailability of cefuroximaxetil from this dosage form is approx. 30% lower than from comparable dosage forms with uncoated particles.

Apart from these difficulties due to the active ingredient, problems sometimes also occur which are determined not only by the active ingredient, but also by the dosage form.

Thus, even when the comparatively readily soluble amorphous cefuroximaxetil is used, in order to ensure sufficient bioavailability it is necessary for the dosage form, for example a film coated tablet, to disintegrate virtually instantaneously on contact with intestinal juice, such that the active ingredient particles may disperse and release the active ingredient rapidly without any appreciable gelation occurring. For this purpose, particles with a small diameter and large specific surface area are conventionally used for the production of film coated tablets.

The twice daily administration of cefuroximaxetil which is in principle desired entails a comparatively high active ingredient loading of the dosage forms. As is known, an elevated active ingredient loading may in particular be achieved with extruded pellets, which moreover comprise the desired smooth, preferably spherical form. A disadvantage of at these dosage forms is, however, that they usually have a very compact structure, which is primarily attributable to auxiliary substances such as microcrystalline cellulose (MCC). Due to their compact structure, these dosage forms do not disintegrate in an aqueous medium or at most disintegrate only very slowly, which may result in unwanted, greatly delayed release of cefuroximaxetil.

As a result, it is possible that release will occur to a considerable extent only in a lower portion of the intestine, so preventing adequate bioavailability of the active ingredient.

This low dissolution rate of the dosage form and the associated delayed release of the cefuroximaxetil is in particular observed when known spheronising agents, such as microcrystalline cellulose, hydroxypropylcellulose, hydroxypropylmethylcellulose are used, which, while indeed giving rise to pellets of the desired shape and with a narrow particle size distribution, result in delayed release of the active ingredient.

This is in particular observed in extruded pellets which have been produced with the assistance of the stated spheronising agents, once an existing coating, which may be resistant to saliva and/or gastric juice and also has a flavour neutralisation function, has dissolved. After the pH-dependent dissolution of the coating in the small intestine, such pellets disintegrate only very slowly, even in the presence of disintegrants and surfactants, so delaying the release of the cefuroximaxetil and limiting bioavailability.

Apart from the in any event comparatively poor disintegration characteristics of such pellets, an additional complicating factor with cefuroximaxetil is that, when the amorphous form of the active ingredient is used, release is complicated by gelation and, when known crystalline modifications are used, release is reduced as a result of their lower solubility. The bioavailability of the active ingredient from such pellets is not satisfactory; pellets are, for example, known which release only 20-30% of the active ingredient after 60 min.

BRIEF SUMMARY OF THE INVENTION

The object of the invention is accordingly to provide a pharmaceutical composition which contains cefuroximaxetil and exhibits advantages relative to prior art compositions. The pharmaceutical composition should be readily processable to yield pharmaceutical dosage forms, in particular extruded pellets. Furthermore, release of cefuroximaxetil from the dosage forms in a aqueous medium with a pH value corresponding to the physiological pH value of the small intestine should proceed as fast as possible in order to ensure elevated bioavailability within the "absorption window".

It has surprisingly been found that this object may be achieved by a pharmaceutical composition comprising cefuroximaxetil and at least one carrageenan selected from the group consisting of κ-carrageenan, λ-carrageenan and ι-carrageenan and, preferably κ-carrageenan.

DETAILED DESCRIPTION OF THE INVENTION

Figure 1:
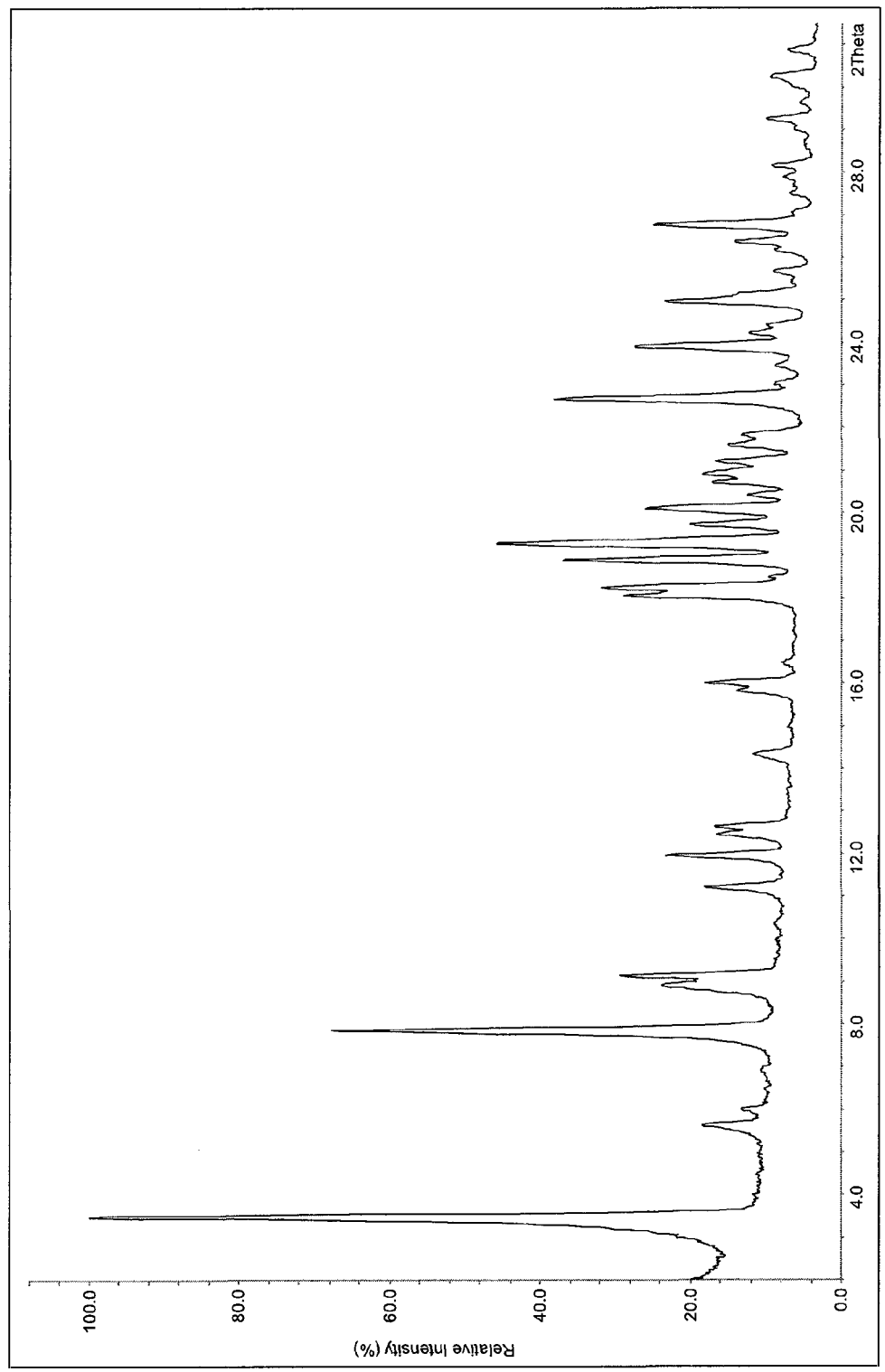
FIG. 1 is an X-ray diffractogram of the novel crystalline modification of cefuroximaxetil (δ-modification).

Carrageenans are sulfated polysaccharides which occur as structural components in the cell walls of specific genera of red algae. κ-Carrageenan may, for example, be isolated from *Kappaphycus alverezii, Chondrus crispus* and *Sarcothalia crispata*.

κ-Carrageenan, λ-carrageenan and ι-carrageenan are polysaccharides which differ in particular with regard to the number and position of sulfate ester groups. Unless otherwise specified, for the purposes of the invention the term "carrageenan" means at least one carrageenan selected from the group consisting of κ-carrageenan, λ-carrageenan and ι-carrageenan.

Chemically, a molecular scaffold of κ-carrageenan may preferably also be designated as "-(1→3)-β-D-galactopyranose-4-sulfate-(1→4)-3,6-anhydro-α-D-galactopyranose-(1→3)-", the molecular scaffold of ι-carrageenan as "-(1→3)-β-D-galactopyranose-4}-sulfate-(1→4)-3,6-anhydro-α-D-galactopyranose-2-sulfate-(1→3)-" and the molecular scaffold of λ-carrageenan as "-(1→3)-β-D-galactopyranose-2-sulfate-(1→4)-α-D-galactopyranose-2,6-disulfate-(1→3)-".

For the purposes of the description, κ-carrageenan preferably includes sulfated polygalactoside substructures which are derived from D-galactose and 3,6-anhydro-D-galactose. Examples of such substructures are:

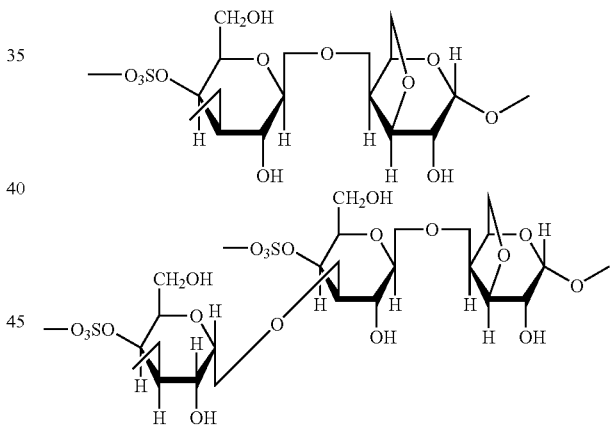

Still further carrageenans are known in the prior art, for example α-carrageenan, β-carrageenan, γ-carrageenan and ε-carrageenan.

The composition according to the invention preferably contains a carrageenan which on average comprises per pyranose unit fewer than 1.5 sulfate equivalents, more preferably less than 1.0 sulfate equivalent and in particular 0.6±0.1 sulfate equivalents.

The composition according to the invention preferably containsκ-carrageenan, preferably as the sodium, potassium or calcium salt. κ-Carrageenan or the salts thereof are commercially obtainable, for example under the name Gelcarin®.

With regard to further details about κ-carrageenan and the specifications of carrageenans, reference may for example be made to T. H. M. Snoeren, *Kappa-carrageenan: A study on its physico-chemical properties, sol-gel transition and interaction with milk proteins* (N.I.Z.O.-verslagen), H. Veenman and Zonen B. V (1976); Uno Y, Omoto T, Goto Y, Asai I, Nakamura M, Maitani T (2001), *Molecular weight distribution of carrageenans studied by a combined gel permeation/inductively coupled plasma (GPC/ICP)method*, Food Additives and Contaminants 18: 763-772; and JECFA (1998), *Compendium of Food Additive Specifications Addendum* 6, pp. 29-33, FAO, Rome.

In one preferred embodiment of the composition according to the invention, the composition contains at least 5.5 wt. %, more preferably at least 6.0 wt. %, still more preferably at least 6.5 wt. %, most preferably at least 7.0 wt. % and in particular at least 7.5 wt. % carrageenan, preferably κ-carrageenan. The composition according to the invention particularly preferably contains 7.5 to 50 wt. %, more preferably 10 to 40 wt. % and in particular 20 to 30 wt. % carrageenan, preferably κ-carrageenan, relative to the total weight of the composition.

The ratio by weight of cefuroximaxetil to carrageenan is preferably in the range from 0.5:1 to 5.0:1, more preferably 1.0:1 to 4.0:1, still more preferably 1.5:1 to 3.5:1, most preferably 2.0:1 to 3.0:1 and in particular 2.2:1 to 2.6:1.

In a preferred embodiment, the composition according to the invention contains tricalcium phosphate and/or at least one sucrose ester. In a particularly preferred embodiment, the composition according to the invention contains both tricalcium phosphate and at least one sucrose ester.

Preferred sucrose esters have a hydrophilicity-lipophilicity balance (HLB) value of 10 to 17, more preferably of 11 to 16, in particular of 13 to 15.

The composition according to the invention preferably contains the sucrose ester in a quantity of 1.0 to 10 wt. %, more preferably of 2.0 to 8.0 wt. % and in particular of 4.0 to 6.0 wt. %, relative to the total weight of the composition.

According to the invention, the sucrose ester preferably comprises sucrose stearate, sucrose palmitate, sucrose laurate, sucrose behenate, sucrose oleate, sucrose erucate or mixtures thereof. It particularly preferably comprises sucrose palmitate, which has an HLB of approx. 15 and is commercially obtainable, for example under the designation "S-1570" from Mitsubishi.

If the composition according to the invention contains tricalcium phosphate and carrageenan, the ratio by weight of tricalcium phosphate to carrageenan preferably amounts to 1:1 to 1:10, in particular 1:2 to 1:6.

The tricalcium phosphate used is preferably a finely divided powder with an average particle size of <50 μm.

The composition according to the invention may contain conventional auxiliary substances, such as for example fillers, binders, slip agents, antioxidants, dyes or preservatives. Such auxiliary substances are known to the person skilled in the art. In this connection, comprehensive reference may be made to H. P. Fiedler, *Lexikon der Hilfsstoffe für Pharmazie, Kosmetik und angrenzende Gebiete*, 2 vols., Editio Cantor, Aulendorff, 2002; D. E. Bugay, *Pharmaceutical Excipients* (*Drugs and the Pharmaceutical Sciences, V.* 94) (Hardcover), CRC, 1998.

In a preferred embodiment, the composition according to the invention contains no microcrystalline cellulose or other spheronisation auxiliaries, such as for example low substituted hydroxypropylcellulose, hydroxypropylmethylcellulose, hydroxymethylcellulose, pulverulent cellulose, sodium carboxymethylcellulose or polyvinylpyrrolidone, provided that they have not yet been provided with a coating as a dosage form.

The composition according to the invention may be further processed to yield a multiparticulate, pharmaceutical dosage form, preferably in the form of extruded pellets which, once an optionally present coating has first dissolved, release at least 85% of the cefuroximaxetil within 30 minutes at a pH value of 6 to 7.

The dissolution rate and thus virtually non-delayed release of the active ingredient is preferably determined according to the method described in "*Guidance for Industry, Waiver of In Vivo Bioavailability and Bioequivalence Studies for Immediate-Release Solid Oral Dosage Forms based on a Biopharmaceutics Classification System.*, pages 1-3/7, publisher U.S. Department of Health and Human Services, Food and Drug Administration, Center for Drug Evaluation and Research (CDER), August 2000, BP".

Such a high dissolution rate is not achieved with the assistance of the extruded pellets known from the prior art and produced using microcrystalline cellulose even if said pellets are provided with a gastric juice resistant and/or flavour-neutral finish. Once the film coating has dissolved, such dosage forms in fact still exhibit delayed disintegration, so delaying release in the small intestine, as in corresponding, uncoated pellets, and consequently impairing the bioavailability thereof.

It is thus all the more surprising that the dosage forms which are produced from the compositions according to the invention, even if provided with a gastric juice resistant coating, for example for flavour neutralisation, exhibit rapid dissolution, once such a coating has dissolved, at a physiological pH value of the small intestine of 6 to 7, and so give rise to the release of preferably at least 85% of the cefuroximaxetil within 30 minutes. Release of at least 85% is particularly preferably achieved within just 15 minutes (rapid release).

The composition according to the invention may thus in particular be used for the production of extrudates which are then converted into rounded pellets by spheronisation. Multiparticulate dosage forms obtained by extrusion which contain cefuroximaxetil, carrageenan, optionally tricalcium phosphate and optionally at least one sucrose ester are thus particularly suitable for the administration of cefuroximaxetil, due to the elevated active ingredient loading which is possible, the reduced requirements for flavour neutralisation and the rapid dissolution rate at a pH value of 6 to 7.

A further aspect of the invention relates to a process for the production of pellets from an above-described pharmaceutical composition, comprising the steps (a) mixing of cefuroximaxetil, preferably a mixture of amorphous cefuroximaxetil and crystalline cefuroximaxetil, preferably the α-modification, at least one carrageenan selected from the group consisting of κ-carrageenan, λ-carrageenan and ι-carrageenan, and optionally further constituents, preferably tricalcium phosphate and/or at least one sucrose ester;

(b) granulation of the mixture obtained in step (a);

(c) extrusion of the granules obtained in step (b) and preferably subsequent subdivision of the resultant extrudate;

(d) optional spheronisation of the extrudate obtained in step (c) and preferably subsequent classification of the resultant pellets; and (e) optional coating of the pellets obtained in step (d) with a gastric juice resistant and/or saliva resistant coating.

Preferred embodiments of the process according to the invention, such as for example preferred quantity ratios of the components used, are described above in connection with the pharmaceutical composition according to the invention.

Steps (d) and (e) of the process according to the invention are optional. The process according to the invention preferably comprises all of steps (a) to (e), such that coated extruded pellets are obtained by the process. These pellets may be provided with conventional gastric juice resistant and/or saliva resistant coatings. Cefuroximaxetil, which exhibits a largely pH-independent solubility of approx. 0.5 mg/ml, is preferably protected with gastric juice resistant coatings. In a preferred embodiment, however, the pellets are not coated with a lipid or a mixture of two or more lipids, which are insoluble in water, but pass into solution on contact with the gastrointestinal fluid. The pellets according to the invention are accordingly, for example, preferably not coated with stearic acid.

The person skilled in the art is aware that the components may be added to the mixture simultaneously or in succession. Mixing may likewise proceed in a known mixer or granulator, such that mixing, granulation and extrusion may optionally proceed simultaneously.

In a preferred embodiment of the process according to the invention, step (b) proceeds as wet granulation. Wet granulation may preferably proceed with water or an aqueous solvent.

Spheronisation, extrusion and coating may in each case proceed in the apparatus known to the person skilled in the art. A fluidised bed-apparatus may preferably be used for coating.

A combination of amorphous cefuroximaxetil and crystalline cefuroximaxetil is preferably used in the process according to the invention. The crystalline cefuroximaxetil preferably comprises the α-modification. The relative ratio by weight of cefuroximaxetil in amorphous form to cefuroximaxetil in crystalline form is here preferably in the range from 10:90 to 90:10, more preferably from 20:80 to 80:20, still more preferably from 30:70 to 70:30 and most preferably from 40:60 to 60:40. The relative ratio by weight particularly preferably amounts to 50:50. This aspect of the invention relates to such a mixture comprising amorphous cefuroximaxetil and cefuroximaxetil in the α-modification, preferably in one of the above-stated relative ratios by weight.

A further aspect of the invention relates to pellets, preferably extruded pellets, which are obtainable by the above-described process. The pellets according to the invention are distinguished by excellent disintegration characteristics in an aqueous medium. They furthermore enable a comparatively high active ingredient loading. Release and thus concomitantly also the bioavailability of cefuroximaxetil from dosage forms which contain the pellets according to the invention, are distinctly improved in comparison with prior art dosage forms. Once an optionally present coating has first dissolved, release of at least 85% within only 30 minutes may preferably be achieved in this manner.

A further aspect of the invention accordingly relates to a solid pharmaceutical dosage form containing cefuroximaxetil, which dosage form, once an optionally present coating has first dissolved, releases the cefuroximaxetil under physiological conditions at a pH value of 6 to 7 in a quantity of at least 75%, preferably of at least 85% within 30 minutes. The dosage form is preferably multiparticulate. Release is here preferably determined as described in connection with the Examples.

A further aspect of the invention furthermore relates to a multiparticulate, pharmaceutical dosage form comprising an above-described pharmaceutical composition, preferably above-described pellets.

Preferred embodiments of the dosage form according to the invention, such as for example preferred quantity ratios of the components used, are described above in connection with the pharmaceutical composition according to the invention or the pellets according to the invention.

The dosage form according to the invention is preferably intended for oral administration. It is preferably multiparticulate. It preferably comprises granules, pellets, preferably extruded pellets, microgranules or micropellets. The dosage form according to the invention particularly preferably assumes the form of extruded pellets, preferably in spherical form. These may optionally be packaged in gelatine capsules.

The particles of the multiparticulate dosage form according to the invention preferably have an average diameter (size) of <1000 μm, more preferably of <900 μm, still more preferably of <800 μm, most preferably of <700 μm and in particular of between 250 and 700 μm.

In a preferred embodiment, the dosage form according to the invention assumes the form of a tablet, in particular a film coated tablet. The tablets are here particularly preferably obtainable by tabletting the pellets according to the invention, preferably extruded pellets, with the addition of conventional tabletting auxiliaries.

In a preferred embodiment of the dosage form according to the invention, it comprises a gastric juice resistant and/or saliva resistant coating. Before this coating is applied, a protective coating which isolates the core is preferably additionally applied.

Depending on the nature and function of these coatings, they are preferably applied in a quantity of 1.0 to 50 wt. %, more preferably of 2.0 to 25 wt. %, relative to the total weight of the dosage forms.

Materials which are suitable for a gastric juice resistant coating are preferably methacrylic acid/alkyl methacrylate copolymers, preferably copolymers of methacrylic acid/methyl methacrylate in a molar ratio of the monomers of 1:1 to 1:2, such as Eudragit L®, Eudragit S® or Eudragit L30D-55®, or ethyl methacrylate, which dissolve rapidly at a pH value of ≥pH 6. Gastric juice resistant coatings which may furthermore be applied are those based on celluloses, which are known to the person skilled in the art. The coatings may be applied with appropriate solutions or dispersions in an organic or aqueous medium, an aqueous medium being preferred. Suitable saliva-resistant coatings are preferably coatings based on Eudragit E, Eudragit EPO.

A person skilled in the art is aware that conventional plasticisers, dyes, slip agents, such as talcum and/or magnesium stearate, should or may be added to known coating materials.

According to the invention, "gastric juice" is taken to mean both the natural composition of gastric juice and the artificial preparations similar to gastric juice (pH 1.2 to 2.0) which are known to the person skilled in the art. Likewise, "release in the small intestine" is taken to mean both release in natural small intestine juice and release in preparations similar to small intestine juice at pH values of 6 to 7, preferably at pH 6.4 to 6.8.

The dosage forms according to the invention are distinguished in that they exhibit an elevated dissolution rate and, once an optionally present coating has first dissolved, the cefuroximaxetil is preferably released to an extent of at least 85% within 30 minutes. The pH-dependent duration of dissolution of such a coating may be determined by simple preliminary testing in appropriate standard buffer solutions.

The active ingredient content of the dosage form according to the invention is preferably adapted to once or twice daily administration to an adult or a paediatric patient. In adults, the daily dose is conventionally in the range from 250 to 1000 mg per day, in children, depending on age and weight, it is conventionally in the range from 80 to 500 mg per day. Each dosage unit of the dosage form according to the invention preferably comprises an equivalent quantity relative to 125, 250 or 500 mg of cefuroxime.

In comparison with prior art dosage forms, the dosage form according to the invention exhibits an improved cefuroximaxetil release profile. In a preferred embodiment, once an optionally present coating has first dissolved, the dosage form according to the invention releases cefuroximaxetil at a pH value of 6 to 7 within 30 minutes in a quantity of at least 75%, preferably of at least 80%, more preferably of at least 85%, most preferably of at least 90% and in particular of at least 95%, determined according to the method described in "*Guidance for Industry, Waiver of In Vivo Bioavailability and Bioequivalence Studies for Immediate-Release Solid Oral Dosage Forms based on a Biopharmaceutics Classification System.*, pages 1-3/7, publisher U.S. Department of Health and Human Services, Food and Drug Administration, Center for Drug Evaluation and Research (CDER), August 2000, BP".

In a particularly preferred dosage form according to the invention, the multiparticulate dosage form assumes the form of spherical extruded pellets. These may preferably be present as a single dose according to an administration system comprising a drinking straw with a preferably mobile barrier device, as is described in WO 03/079957, WO 2004/000202, WO2004/000264. The barrier device is preferably a plug, the cross-section of which is preferably adapted to the cross-section of the drinking straw. The plug may be mobile between two limit stops. The drinking straw is narrowed by these limit stops, wherein the narrowed portions are designed such that the plug, but not the multiparticulate dosage form, is retained thereby. Administration to patients preferably proceeds with a conveying liquid.

The descriptions of the administration systems in the stated publications are hereby introduced as a reference and are deemed to be part of the present disclosure.

The present invention also provides an administration system comprising a dosage form according to the invention, preferably as a single dose, arranged in a drinking straw with at least one preferably mobile barrier device for administration to human patients with the assistance of a conveying liquid.

Suitable conveying liquids are particle-free beverages, preferably aqueous liquids, such as for example water, tea, fruit juices, Coca-Cola, lemonade, wherein, when multiparticulate dosage forms, for example extruded pellets, provided with a gastric resistant finish, i.e. coating, are used, conveying liquids with an acidic pH value are preferred.

A further aspect of the invention relates to a novel crystalline modification of cefuroximaxetil ("δ-modification").

It has surprisingly been found that a novel crystalline modification of cefuroximaxetil arises over the course of the process according to the invention for the production of pellets, preferably extruded pellets, from the composition according to the invention. It has proved possible to provide confirmation of this by X-ray diffractometry.

A novel crystalline modification is obtained during the formulation of amorphous cefuroximaxetil, of crystalline cefuroximaxetil of one of the known crystalline modifications or of mixtures of the amorphous form and a known crystalline modification, preferably of the α-modification, in presence of carrageenan, preferably κ-carrageenan. Virtually complete conversion of the forms/modifications used into the novel crystalline modification may be observed if the amorphous form of cefuroximaxetil and crystalline cefuroximaxetil of the α-modification are formulated in the ratio by weight 50:50 in the presence of κ-carrageenan by the process according to the invention to yield extruded pellets.

If granulation proceeds as wet granulation in an aqueous medium, comparatively large quantities of water are necessary, wherein the presence of the crystalline α-modification in addition to the amorphous form simplifies handling of the composition during pellet production.

In order to differentiate the novel crystalline modification of cefuroximaxetil terminologically from the modifications (α, β, γ) hitherto known in the prior art, the novel crystalline modification is hereinafter also designated as the "δ-modification".

The novel crystalline modification preferably arises when a mixture of amorphous cefuroximaxetil and crystalline cefuroximaxetil, preferably of the α-modification, together with carrageenan, preferably κ-carrageenan, are processed to yield pellets, preferably extruded pellets.

It has proved possible to demonstrate by X-ray diffractometry that, over the course of the process, the diffraction reflections caused by the crystalline starting material, i.e. for example by the α-modification, disappear and instead new diffraction reflections occur in the diffractogram, which cannot be assigned to any hitherto known crystalline modification of cefuroximaxetil. To this end, powder diffractograms of the starting mixture (step (a)), of the granules (step (b)), of the extrudate (step (c)) and of the pellets (step (d)) were recorded. It has also proved possible to rule out by comparison measurements that the newly occurring diffraction reflections are caused by the other constituents which may sometimes be used in the production of the pellets, such as for example tricalcium phosphate and/or sugar esters. It would thus appear that, under the conditions of pellet production, a phase transformation of the amorphous form and/or of the crystalline modification occurs which results in the novel crystalline modification according to the invention. The particle size of the starting material does not appear to play any significant role in this connection.

It has moreover surprisingly been found that the δ-modification of cefuroximaxetil according to the invention may also be produced by suspending the α-modification or a 1:1 mixture of the α-modification and the amorphous form in water and stirring at room temperature for a period of several hours, preferably of several days, preferably at room temperature or a slightly elevated temperature, for example at 40° C.

It has furthermore surprisingly been found that the δ-modification of cefuroximaxetil according to the invention may also be produced by precipitation of a solution of the α-modification in acetone by addition of water. To this end, a filtered solution of the α-modification in acetone may initially be introduced and precipitation of the δ-modification induced by slow addition of water. The quantity of water used here preferably amounts to at least the same, more preferably to at least one and a half times and still more preferably to at least twice the quantity of acetone used.

By means of the above-described process, it is straightforwardly possible to produce the δ-modification of cefuroximaxetil according to the invention in virtually pure form on both a gram and a kilogram scale.

One aspect of the invention accordingly also relates to a crystalline modification of cefuroximaxetil which is obtainable by the above-stated process.

An X-ray diffractogram of the novel crystalline modification of cefuroximaxetil (δ-modification) is shown in FIG. 1. The modification according to the invention is in particular characterised by an X-ray diffraction spectrum comprising one or more reflections selected from among 8.3, 10.4, 13.0, 16.4, and 25.5 (°2θ±0.2). A corresponding X-ray diffractogram preferably additionally comprises the following X-ray reflections (°2θ±0.2): 7.3, 14.5, 18.3, 21.1, 21.8 and/or 29.0.

Figure 2:
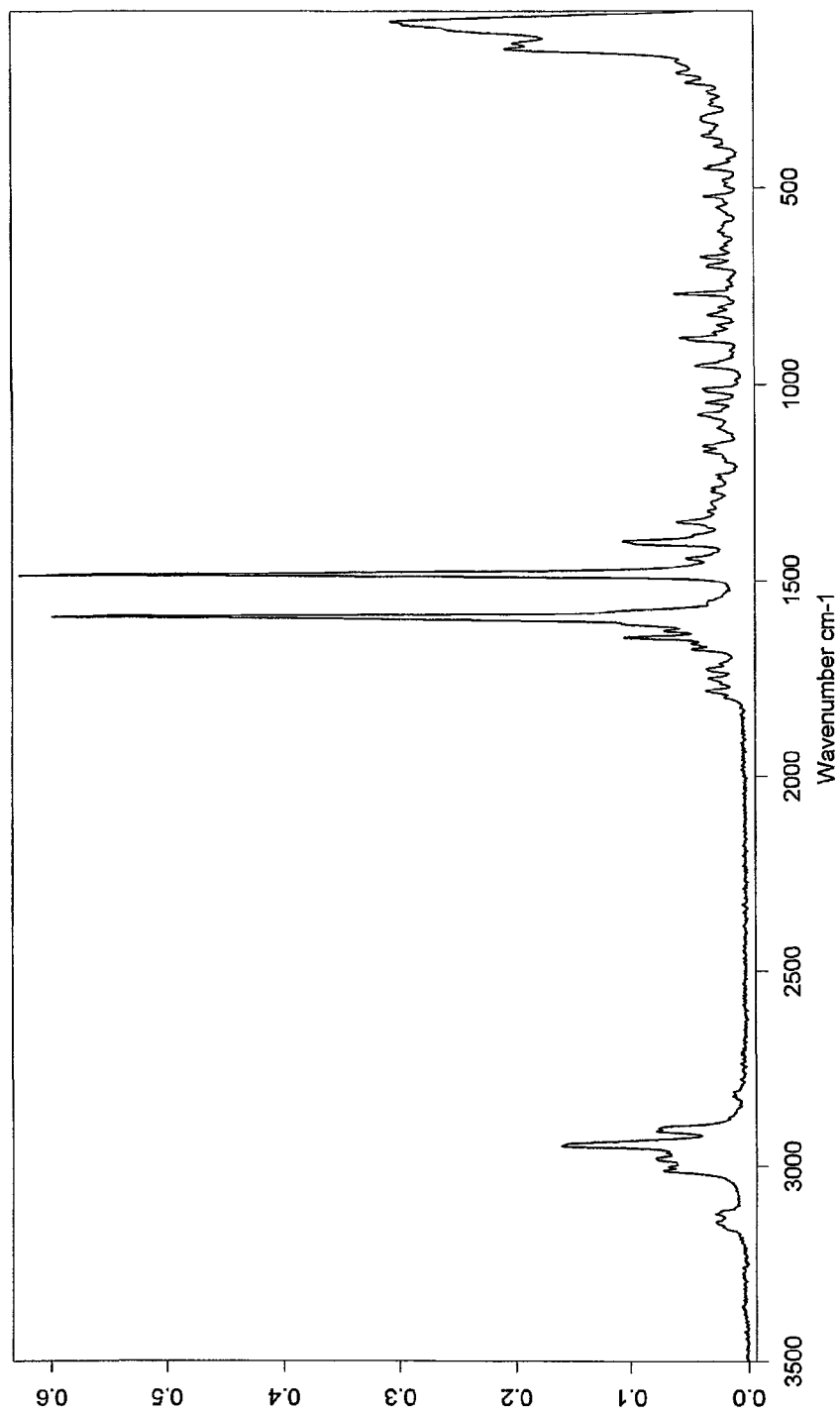
FIG. 2 is an FT Raman spectrum of the novel crystalline modification of cefuroximaxetil (δ-modification)

An FT Raman spectrum of the novel crystalline modification of cefuroximaxetil (δ-modification) is shown in FIG. 2.

The modification according to the invention is in particular characterised by an FT Raman spectrum comprising one or more peaks selected from among 1676, 1646, 1629 and 1593 (±3 cm$^{-1}$). A corresponding FT Raman spectrum preferably additionally comprises the following peaks: 2948, 1781, 1485, 1398, 1076, 881 and/or 767 (±3 cm$^{-1}$).

The crystalline modification of cefuroximaxetil according to the invention has advantages over hitherto known crystalline modifications of cefuroximaxetil. On the one hand, the specific physical properties of the modification may be of interest during processing and storage (thermodynamic stability, morphology, colour, density, bulk density, melting point, solubility characteristics, hygroscopicity, tackiness, hardness, deformability, etc.). On the other hand, the crystalline modification may also exhibit improved chemical properties. For example, it is known that lower hygroscopicity may result in improved chemical stability and a longer storage life of chemical compounds.

In particular, the modification according to the invention exhibits improved dissolution or release behaviour and thus improved bioavailability of the active ingredient. Pellets which have been produced by the process according to the invention or contain the crystalline modification of cefuroximaxetil according to the invention accordingly exhibit almost complete active ingredient release after only 20 to 30 minutes, indeed largely independently of the modification and particle size of the cefuroximaxetil which was used for pellet production.

This rapid active ingredient release is still obtained if the pellets are provided with a coating and release is measured once the coating has dissolved.

The crystalline modification of cefuroximaxetil according to the invention is stable in storage. After storage at elevated temperature, no significant change to the composition can be observed, whether chemically (decomposition products) or physically (solubility, X-ray diffractogram). Even after storage for 2 months at 40° C. and 75% rel. atmospheric humidity, the content of the comparatively easily formed $\Delta^3$-degradation product is still below 1.0 wt. %, which is indicative of excellent stability of the modification according to the invention.

With the assistance of binary mixtures of the α-, β-, γ- and δ-modification in water, it has been possible to demonstrate that the δ-modification according to the invention is stabler under these conditions than the α-, β- and γ-modification.

The stability of the modification is a highly significant aspect in polymorphism. By using the stable modification in the pharmaceutical preparation, it is in fact possible to ensure that no polymorphic transformation occurs in the formulation during storage. This is of particular significance because the transformation of a less stable modification into a stabler modification may otherwise modify the properties of the pharmaceutical preparation.

Because the modification according to the invention already provides a modification which is stabler than hitherto known modifications, transformation into the hitherto known, less stable modifications can be ruled out on thermodynamic grounds.

This aspect becomes additionally significant due to the fact that, apart from the amorphous modification, cefuroximaxetil including the crystalline δ-modification according to the invention is already known to have three further crystalline modifications (α-, β- and γ-). Cefuroximaxetil is in fact clearly distinguished by a marked tendency towards polymorphism, which is not the case for every pharmaceutical substance. Due to the comparatively large number of metastable modifications, polymorphic transformation during storage is, however, more probable in principle. In such cases, therefore, there is a particular requirement to provide the stablest possible polymorphic modification.

The following Examples serve to illustrate the invention in greater detail, but should not be interpreted restrictively with regard to the scope thereof.

The release rate of cefuroximaxetil was determined according to the method described in "*Guidance for Industry, Waiver of In Vivo Bioavailability and Bioequivalence Studies for Immediate-Release Solid Oral Dosage Forms based on a Biopharmaceutics Classification System.*, pages 1-3/7, publisher U.S. Department of Health and Human Services, Food and Drug Administration, Center for Drug Evaluation and Research (CDER), August 2000, BP".

A release apparatus with paddle stirrer according to U.S. Pharmacopeia was used for this purpose and release was measured at a temperature of 37° C. and a rotational speed of 150 min$^{-1}$ in 1000 ml of artificial intestinal juice (sodium phosphate buffer, pH 6.8) and 0.3% SDS or in 1000 ml of artificial gastric juice (pH 1.2) and 0.5% Tween 80 as release medium in the time stated in the Examples. The particular quantity of active ingredient released at any one time was determined by HPLC. Detection was by means of a UV detector at 282 nm. The average from 6 measurements was calculated.

EXAMPLE 1

Extruded Pellets of the Following Composition were Produced:

| Equivalent quantity of cefuroxime per 250 mg | Constituent | Total |
|---|---|---|
| 150.5 mg | Cefuroximaxetil, microcrystalline, α-modification | 119.04 g |
| 150.5 mg | Cefuroximaxetil, amorphous | 119.04 g |
| 60.2 mg | Tricalcium phosphate | 47.62 g |
| 120.4 mg | Gelcarin | 95.24 g |
| 24.1 mg | Sugar ester S-1570 | 19.06 g |
| 505.7 mg | Total | 400.00 g |

To this end, all the constituents were mixed in a Diosna mixer and wet granulated in this mixer. The moist granules were extruded in a Nica E142 extruder with a 0.5×0.5 mm die. The resultant extrudates were spheronised in a Nica S450 spheroniser. The resultant pellets were dried in a fluidised bed at 50° C. and then classified. Uncoated pellets with a particle diameter of 250-710 μm were used for determining cefuroximaxetil release.

Release was determined both in artificial gastric juice+Tween, and in artificial intestinal juice+SDS with in each case approx. 253 mg of uncoated pellets (total content of cefuroximaxetil approx. 150 mg, corresponds to equivalent quantity of 125 mg of cefuroxime, dosage unit for children).

In the case of artificial gastric juice, the measurement was repeated after storing the pellets for 2 months at 40° C.:

a) Artificial Gastric Juice+Tween 80:

|  | Average in % | |
|---|---|---|
| after | immediately after production | after 2 months' storage at 40° C. |
| 30 min | 83.8 | 85.2 |
| 60 min | 83.9 | 85.4 |
| 90 min | 84.2 | 85.4 |
| 120 min | 84.3 | 85.2 | b) Artificial Intestinal Juice+SDS:

| after | |
|---|---|
| 15 min | 75.6 |
| 30 min | 86.2 |
| 45 min | 89.2 |
| 60 min | 90.7 |

As the above data demonstrate, the excellent release rate of the compositions according to the invention is achieved both in artificial gastric juice and in artificial intestinal juice. This sometimes appears to be attributable to the fact that the solubility of cefuroximaxetil is largely independent of the pH value.

The Following Impurities and Decomposition Products could be Identified by HPLC Analysis [%]:

|  | immediately after production | after 2 months' storage at 40° C. |
|---|---|---|
| Cefuroxime Δ[3] | 0.39 | 0.45 |
| Cefuroxime A (E) isomer | 0.20 | 0.19 |
| Cefuroxime B (E) isomer | 0.22 | 0.24 |
| Σ unknown impurities | 0.56 | 0.52 |
| Σ all impurities | 1.37 | 1.40 |

EXAMPLE 2

Pellets of the Following Composition were Produced in a Similar Manner to Example 1:

| Equivalent quantity of cefuroxime per 250 mg | Constituent | Total |
|---|---|---|
| 150.5 mg | Cefuroximaxetil, microcrystalline, α-modification | 129.18 g |
| 150.5 mg | Cefuroximaxetil, amorphous | 129.18 g |
| 34.0 mg | Tricalcium phosphate | 29.19 g |
| 131.0 mg | Gelcarin | 112.45 g |
| 466.0 mg | Total | 400.00 g |

Release of an Equivalent Dose of 125 or 62.5 mg of Cefuroxime in Artificial Gastric Juice+Tween 80:

|  | Average in % | |
|---|---|---|
| after | 125 mg cefuroxime | 62.5 mg cefuroxime |
| 30 min | 83.9 | 103.0 |
| 60 min | 83.9 | 103.2 |
| 90 min | 84.3 | 103.1 |
| 120 min | 84.4 | 102.7 |

The more rapid release at a dose of 62.5 mg is due to cefuroximaxetil's saturation solubility of 600 mg in the dissolution medium (1000 ml). Sink conditions may accordingly only be assumed up to a test dose of approx. 60 mg (max. 10% of the saturation solubility).

EXAMPLE 3

Pellets of the Following Composition were Produced in a Similar Manner to Example 1:

| Equivalent quantity of cefuroxime per 250 mg | Constituent | Total |
|---|---|---|
| 301.0 mg | Cefuroximaxetil, amorphous | 119.04 g |
| 60.2 mg | Tricalcium phosphate | 23.81 g |
| 120.4 mg | Gelcarin | 47.62 g |
| 24.1 mg | Sugar ester S-1570 | 9.53 g |
| 505.7 mg | Total | 200.00 g |

Release in Artificial Gastric Juice+0.5% Tween 80 (Quantity used Corresponding to an Equivalent Dose of 125 mg of Cefuroxime):

| after | Average in % |
|---|---|
| 30 min | 95.6 |
| 60 min | 100.4 |
| 90 min | 100.9 |
| 120 min | 101.0 |

EXAMPLE 4

Pellets of the Following Composition were Produced in a Similar Manner to Example 1:

| Equivalent quantity of cefuroxime per 250 mg | Constituent | Total |
|---|---|---|
| 301.0 mg | Cefuroximaxetil, crystalline, α-modification | 119.04 g |
| 60.2 mg | Tricalcium phosphate | 23.81 g |
| 120.4 mg | Gelcarin | 47.62 g |
| 24.1 mg | Sugar ester S-1570 | 9.53 g |
| 505.7 mg | Total | 200.00 g |

Release in Artificial Gastric Juice+0.5% Tween 80:

| after | Average in % | |
|---|---|---|
| | 125 mg cefuroxime | 62.5 mg cefuroxime |
| 30 min | 82.9 | 101.7 |
| 60 min | 83.4 | 101.5 |
| 90 min | 83.8 | 101.3 |
| 120 min | 84.1 | 101.1 |

As this test shows, complete dissolution of the cefuroximaxetil contained in the pellets according to the invention at a total quantity which corresponds to an equivalent dose of 125 mg of cefuroxime may be limited by the volume of the release medium used, in this case 1000 ml of artificial gastric juice. Quantitative release is achieved in those cases in which the quantity of active ingredient is reduced with a constant release volume. This situation is of no physiological significance because, under physiological conditions, the release medium is constantly replenished by the body.

EXAMPLE 5

Pellets of the Following Composition were Produced in a Similar Manner to Example 1:

| Equivalent quantity of cefuroxime per 250 mg | Constituent | Total |
|---|---|---|
| 240.8 mg | Cefuroximaxetil, microcrystalline, α-modification | 95.233 g |
| 60.2 mg | Cefuroximaxetil, amorphous | 23.809 g |
| 60.2 mg | Tricalcium phosphate | 23.808 g |
| 120.4 mg | Gelcarin | 47.620 g |
| 24.1 mg | Sugar ester S-1570 | 9.531 g |
| 505.7 mg | Total | 200.00 g |

EXAMPLE 6

Pellets of the Following Composition were Produced in a Similar Manner to Example 1:

| Equivalent quantity of cefuroxime per 250 mg | Constituent | Total |
|---|---|---|
| 60.2 mg | Cefuroximaxetil, microcrystalline, α-modification | 23.809 g |
| 240.8 mg | Cefuroximaxetil, amorphous | 95.233 g |
| 60.2 mg | Tricalcium phosphate | 23.808 g |
| 120.4 mg | Gelcarin | 47.620 g |
| 24.1 mg | Sugar ester S-1570 | 9.531 g |
| 505.7 mg | Total | 200.00 g |

EXAMPLE 7

Pellets of the Following Composition were Produced in a Similar Manner to Example 1:

| Equivalent quantity of cefuroxime per 250 mg | Constituent | Total |
|---|---|---|
| 150.5 mg | Cefuroximaxetil, microcrystalline, α-modification, average particle size <25 μm | 1505.0 g |
| 150.5 mg | Cefuroximaxetil, amorphous | 1505.0 g |
| 60.2 mg | Tricalcium phosphate | 602.0 g |
| 120.4 mg | Gelcarin GP911 | 1204.0 g |
| 24.1 mg | Sugar ester S-1570 | 241.0 g |
| 505.7 mg | Total | 5057.0 g |

Release in Artificial Gastric Juice+0.5% Tween 80 (Equivalent Quantity Corresponding to 125 mg of Cefuroxime):

| after | Average in % |
|---|---|
| 30 min | 87.8 |
| 60 min | 87.8 |
| 90 min | 87.9 |
| 120 min | 87.8 |

Impurities and Decomposition Products [%]:

| | |
|---|---|
| Cefuroxime $\Delta^3$ | 0.29 |
| Cefuroxime A (E) isomer | 0.19 |
| Cefuroxime B (E) isomer | 0.19 |
| Cefuroxime acid A isomer | 0.00 |
| Cefuroxime acid B isomer | 0.04 |
| Cefuroxime acid | 0.30 |
| $\Sigma$ unknown impurities | 0.13 |
| $\Sigma$ all impurities | 0.79 |

EXAMPLE 8

Pellets of the Following Composition were Produced in a Similar Manner to Example 1:

| Equivalent quantity of cefuroxime per 250 mg | Constituent | Total |
|---|---|---|
| 150.5 mg | Cefuroximaxetil, microcrystalline, α- modification, average particle size <10 μm | 1505.0 g |
| 150.5 mg | Cefuroximaxetil, amorphous | 1505.0 g |
| 60.2 mg | Tricalcium phosphate | 602.0 g |
| 120.9 mg | Gelcarin GP911 | 1204.0 g |
| 24.1 mg | Sugar ester S-1570 | 241.0 g |
| 505.7 mg | Total | 5057.0 g |

Release in Artificial Gastric Juice+0.5% Tween 80 (Equivalent Quantity Corresponding to 125 mg of Cefuroxime:

| after | Average in % |
|---|---|
| 30 min | 88.9 |
| 60 min | 88.9 |
| 90 min | 88.8 |
| 120 min | 88.8 |

Impurities and Decomposition Products [%]:

| | |
|---|---|
| Cefuroxime $\Delta^3$ | 0.27 |
| Cefuroxime A (E) isomer | 0.13 |
| Cefuroxime B (E) isomer | 0.20 |
| Cefuroxime acid A isomer | 0.00 |
| Cefuroxime acid B isomer | 0.02 |
| Cefuroxime acid | 0.20 |
| Σ unknown impurities | 0.20 |
| Σ all impurities | 0.80 |

EXAMPLE 9

(coated with 5% Eudragit EPO for flavour masking, 5% hypromellose, hydroxypropylmethylcellulose, sub-coat of TiO$_2$, Macrogol 6000)

The Pellets from Example 1 were Coated with a Film of the Following Composition:

| Equivalent quantity of cefuroxime per 250 mg | Constituent | wt. % |
|---|---|---|
| 50.27 g | Eudragit EPO | 10.05 |
| 5.00 g | SLS | 1.00 |
| 7.55 g | Stearic acid | 1.51 |
| 437.10 g | Purified water | 87.42 |
| 499.92 g | Total | 100.00 |

Solids content: 12.58 wt. %

The coating was applied by aqueous coating in a fluidised bed at a production temperature of 30° C.

Impurities and Decomposition Products [%]:

| | |
|---|---|
| Cefuroxime $\Delta^3$ | 0.54 |
| Cefuroxime A (E) isomer | 0.21 |
| Cefuroxime B (E) isomer | 0.20 |
| Cefuroxime acid A isomer | 0.00 |
| Cefuroxime acid B isomer | 0.05 |
| Cefuroxime acid | 0.33 |
| Σ unknown impurities | 0.22 |
| Σ all impurities | 1.17 |

Release in Artificial Gastric Juice+0.5% Tween 80 (Equivalent Quantity Corresponding to 125 mg of Cefuroxime):

| after | Average in % |
|---|---|
| 30 min | 81.5 |
| 60 min | 82.2 |
| 90 min | 82.4 |
| 120 min | 82.8 |

Measurement here started at time 0. The coating dissolved completely after 5 minutes.

EXAMPLE 10

(coated with 15% Eudragit L-55 for flavour masking, 10% hydroxypropylmethylcellulose coating similar to Example 9)

The Pellets from Example 8 were Coated with a Film of the Following Composition:

| Equivalent quantity of cefuroxime per 250 mg | Constituent | wt. % |
|---|---|---|
| 1085.75 g | Eudragit L30 D55 | 43.43 |
| 8.25 g | GMS (glycerol monostearate) | 0.33 |
| 41.00 g | TEC (triethyl citrate) | 1.64 |
| 0.25 g | Polysorbate 80 | 0.01 |
| 1364.75 g | Purified water | 54.59 |
| 2500.00 g | Total | 100.00 |

Solids content: 15 wt. %

Coating was performed in a fluidised bed at a production temperature of 30° C. in a quantity such that the coating constituted 15 wt. % of the coated pellets (15% wt./wt.).

Impurities and Decomposition Products [%]:

| | |
|---|---|
| Cefuroxime $\Delta^3$ | 0.28 |
| Cefuroxime A (E) isomer | 0.16 |
| Cefuroxime B (E) isomer | 0.19 |
| Cefuroxime acid A isomer | 0.00 |
| Cefuroxime acid B isomer | 0.00 |
| Cefuroxime acid | 0.26 |
| Σ unknown impurities | 0.20 |
| Σ all impurities | 0.82 |

Measurement of release in artificial gastric juice (30 minutes, pH 2, 300 ml) and then in artificial intestinal juice (45 minutes, pH 6.8, 1000 ml, 100 rpm) yields the following results:

| after | |
|---|---|
| 30 min | 0.5% |
| 40 min | 98.9% |
| 50 min | 100.8% |
| 60 min | 103.4% |

EXAMPLE 11

The crystalline modification of cefuroximaxetil according to the invention was characterised by X-ray diffractometry. An X-ray powder diffractogram (XRPD) was recorded for this purpose and is reproduced in FIG. 1.

Characteristic reflections (°2θ values) of the known α-modification and the modification according to the invention are compared below:

| α-Modification | |
|---|---|
| °2θ | I/I1 |
| 3.48 | 100 |
| 5.62 | 18 |
| 5.99 | 13 |
| 7.85 | 68 |
| 8.92 | 24 |
| 9.14 | 29 |
| 11.21 | 18 |
| 11.95 | 23 |
| 12.45 | 17 |
| 12.62 | 16 |
| 14.31 | 11 |
| 15.83 | 14 |
| 16.00 | 18 |
| 16.47 | 8 |
| 18.06 | 29 |
| 18.89 | 37 |
| 19.29 | 46 |
| 19.72 | 20 |
| 20.10 | 26 |
| 20.72 | 17 |
| 20.92 | 18 |
| 21.59 | 15 |
| 22.68 | 38 |
| 23.46 | 9 |
| 23.91 | 28 |
| 24.97 | 24 |
| 25.67 | 9 |
| 26.18 | 9 |
| 26.37 | 14 |
| 26.77 | 25 |
| 27.51 | 7 |
| 27.89 | 8 |
| 28.16 | 9 |
| 29.25 | 10 |

| Modification according to the invention | |
|---|---|
| °2θ | I/I1 |
| 3.46 | 100 |
| 7.27 | 22 |
| 8.31 | 30 |
| 9.11 | 39 |
| 10.43 | 26 |
| 11.95 | 44 |
| 12.41 | 25 |
| 12.95 | 26 |
| 14.53 | 20 |
| 15.94 | 35 |
| 16.38 | 26 |
| 18.26 | 45 |
| 18.88 | 50 |
| 20.12 | 31 |
| 20.66 | 36 |
| 21.11 | 33 |
| 21.59 | 27 |
| 21.83 | 26 |
| 22.65 | 42 |
| 24.94 | 30 |
| 25.52 | 26 |
| 29.03 | 16 |

The modification according to the invention of cefuroximaxetil is characterised by one or more of the following X-ray reflections (°2θ±0.2), which are measured during a powder recording at room temperature and Cu $K_\alpha$ radiation: 8.3, 10.4, 13.0, and 25.5. Such an X-ray diffractogram additionally preferably comprises the following X-ray reflections (°2θ±0.2): 7.3, 14.5, 18.3, 21.1, 21.8 and 29.0.

The X-ray diffractograms were recorded as powder recordings with an STOE Stadi P powder diffractometer. The instrument was equipped with a curved germanium monochromator and a linear position-selective detector. The samples were prepared as flat samples. The radiation source used was a copper X-ray tube with monochromatic Cu $K_{\alpha 1}$ radiation (λ=1.54051 Å), produced at 50 kV and 30 mA. The diffraction reflections were measured over an angular range of 2° to 50°. Step width was 0.05°. Measurement was performed at 23±1° C.

EXAMPLE 12

Production of the δ-Modification of Cefuroximaxetil According to the Invention in the Absence of Auxiliary Substances a) Approx. 1 g of a 1:1 mixture of the α-modification and the amorphous form of cefuroximaxetil was placed in a vessel and combined with approx. 2-3 ml of water. A suspension formed, which was stirred in the sealed vessel for 48 h at room temperature. Once the liquid had been filtered off, the desired crystallisation product remained as a solid residue.

b) 50 mg of the α-modification and 50 mg of the amorphous form of cefuroximaxetil were mixed and stirred for 2 days at room temperature in 3 ml of water. The resultant solid was filtered out and dried under a vacuum. The δ-modification was obtained.

c) 1.0 g of the α-modification of cefuroximaxetil was stirred for 3 hours at 40° C. in 10 ml of water. The resultant solid was filtered out, washed with water and dried under a vacuum at 40° C. The δ-modification was obtained.

d) 485.0 mg of the α-modification of cefuroximaxetil were dissolved in 10 ml of acetone. The solution was filtered and 22 ml of water were gradually added. The resultant suspension was stirred overnight. The precipitate was filtered out and dried under a vacuum at 40° C. The δ-modification was obtained.

The invention claimed is:

1. A rapid release cefuroximaxetil pharmaceutical dosage form comprising extruded pellets comprising:
    cefuroximaxetil;
    20 to 30 wt.-% κ-carrageenan, relative to the total weight of the extruded pellets;
    tricalcium phosphate; and
    1 to 10 wt.-% of sucrose ester relative to the total weight of the extruded pellets;
wherein the weight ratio of cefuroximaxetil to κ-carrageenan is in the range from 1.5:1 to 3.5:1;
wherein the weight ratio of tricalcium phosphate to κ-carrageenan is in the range from 1:1 to 1:10; and
wherein said dosage form releases at least 75% of the cefuroximaxetil within 30 minutes upon exposure to aqueous medium at a pH of 6 to 7.

2. The dosage form as claimed in claim 1, wherein said dosage form is further provided with a flavor masking, saliva resistant or gastric juice resistant coating which dissolves under physiological conditions prevailing in the small intestine, whereby the release time of the cefuroximaxetil is measured commencing from exposure of the pellets upon dissolution of the coating.

3. The dosage form as claimed in claim 1, wherein the sucrose ester has a hydrophilicity-lipophilicity balance (HLB) value of 10 to 17.

4. The dosage form as claimed in claim 1, wherein said cefuroximaxetil is formed from a mixture of amorphous cefuroximaxetil and crystalline cefuroximaxetil in a weight ratio of from 5:95 to 95:5 of amorphous cefuroximaxetil to crystalline cefuroximaxetil.

5. The dosage form as claimed in claim 4, wherein the crystalline cefuroximaxetil is α-crystalline cefuroximaxetil and the weight ratio of amorphous cefuroximaxetil to α-crystalline cefuroximaxetil is in the range from 40:60 to 60:40.

6. The dosage form as claimed in claim 1, wherein said dosage form has an average particle size of less than 800 μm.

7. The dosage form as claimed in claim 1, wherein said dosage form is arranged in a drinking straw with at least one barrier device for single administration.

8. The dosage form as claimed in claim 7, wherein said dosage form is packaged in a kit together with a container containing a physiologically acceptable conveying liquid with a pH of ≤6.

9. A method of producing a rapid release cefuroximaxetil pharmaceutical dosage form comprising:
(a) mixing
cefuroximaxetil,
20 to 30 wt.-% κ-carrageenan, relative to the total weight of the extruded pellets;
tricalcium phosphate; and
1 to 10 wt.-% of sucrose ester relative to the total weight of the extruded pellets;
wherein the weight ratio of cefuroximaxetil to κ-carrageenan is in the range from 1.5:1 to 3.5:1; and
wherein the weight ratio of tricalcium phosphate to κ-carrageenan is in the range from 1:1 to 1:10;
(b) granulating the mixture obtained in step (a) to obtain granules;
(c) extruding the granules obtained in step (b) to form extruded pellets; and
(d) optionally spheronizing the extruded pellets obtained in step (c) to obtain spherical pellets
wherein said dosage form releases at least 75% of the cefuroximaxetil within 30 minutes upon exposure to aqueous medium at a pH of 6 to 7.

10. The method as claimed in claim 9, further comprising coating the pellets with a gastric juice resistant coating or saliva resistant coating.

11. The method as claimed in claim 9, wherein step (b) is performed as wet granulation or as aqueous wet granulation.

12. The method as claimed in claim 9, wherein the cefuroximaxetil is a mixture of amorphous cefuroximaxetil and crystalline cefuroximaxetil in a weight ratio of from 5:95 to 95:5 of amorphous cefuroximaxetil to crystalline cefuroximaxetil.

13. The method as claimed in claim 9, wherein said pellets have an average particle size of less than 800 μm.

* * * * *